(12) United States Patent
Richwin et al.

(10) Patent No.: US 7,414,237 B2
(45) Date of Patent: Aug. 19, 2008

(54) OPTOELECTRONIC SENSOR DEVICE FOR A MOTOR VEHICLE

(75) Inventors: Matthias Richwin, Dortmund (DE); Thomas Weber, Ludenscheid (DE)

(73) Assignee: Leopold Kostal GmbH & Co. KG, Ludenscheid (DE)

( * ) Notice: Subject to any disclaimer, the term of this patent is extended or adjusted under 35 U.S.C. 154(b) by 0 days.

(21) Appl. No.: 11/640,684

(22) Filed: Dec. 18, 2006

(65) Prior Publication Data

US 2007/0096015 A1 May 3, 2007

Related U.S. Application Data

(63) Continuation of application No. PCT/EP2005/007471, filed on Jul. 9, 2005.

(30) Foreign Application Priority Data

Jul. 13, 2004 (DE) .................. 10 2004 033 734

(51) Int. Cl.
*G02B 6/42* (2006.01)
*H01J 5/02* (2006.01)
*G01N 15/06* (2006.01)

(52) U.S. Cl. .................. 250/227.25; 250/239; 250/574

(58) Field of Classification Search .................. 250/216, 250/227.25, 239, 574; 340/602; 73/29.01, 73/73, 293; 356/436; 318/643
See application file for complete search history.

(56) References Cited

U.S. PATENT DOCUMENTS

| 4,652,745 | A | * | 3/1987 | Zanardelli | ............... 250/227.25 |
| 4,701,613 | A | | 10/1987 | Watanabe et al. | |
| 5,661,303 | A | * | 8/1997 | Teder | ....................... 250/341.8 |

FOREIGN PATENT DOCUMENTS

| DE | 44 06 398 A1 | 8/1995 |
| DE | 197 01 258 A1 | 7/1997 |
| DE | 197 20 874 A1 | 11/1998 |
| DE | 198 30 120 A1 | 2/1999 |
| DE | 102 61 101 A1 | 7/2004 |
| JP | 02001318398 A | * 5/2000 |
| WO | WO 02/06095 A1 | 1/2002 |

\* cited by examiner

*Primary Examiner*—Georgia Y. Epps
*Assistant Examiner*—Don Williams
(74) *Attorney, Agent, or Firm*—Brooks Kushman P.C.

(57) ABSTRACT

A sensor for detecting moisture on a pane includes a coupler having prisms arranged in coupling areas for coupling light from a transmitter into the pane at an input angle and prisms arranged in decoupling areas for decoupling light reflected from the pane to a receiver at a corresponding output angle. The prisms in the coupling areas have prism surfaces perpendicular to the input angle and the prisms in the decoupling areas have prism surfaces perpendicular to the output angle. Each prism includes a prism flank. The prism flanks in the decoupling areas may be arranged parallel to the output angle. Some of the prism flanks in the decoupling areas are opaque or roughened. Alternatively, some of the prism flanks in the decoupling areas are tilted from running parallel to the output angle. Alternatively, some of the prism flanks in the decoupling areas include at least one additional superimposed prism.

20 Claims, 3 Drawing Sheets

OPTOELECTRONIC SENSOR DEVICE FOR A MOTOR VEHICLE

CROSS-REFERENCE TO RELATED APPLICATIONS

This is a continuation of International Application PCT/EP2005/007471, published in German, with an international filing date of Jul. 9, 2005, which claims priority to DE 10 2004 033 734.9, filed Jul. 13, 2004, the disclosures of which are both hereby incorporated by reference.

BACKGROUND OF THE INVENTION

1. Field of the Invention

The present invention generally relates to an optoelectronic sensor for detecting moisture on a window and, more particularly, to such an optoelectronic sensor having a prism structure which couples radiation from a transmitter into the window and decouples reflected radiation out of the window towards a receiver in which the prism structure includes individual prisms having prism surfaces in coupling areas arranged perpendicular to the input radiation angle of incidence and prism surfaces in decoupling areas arranged perpendicular to the output radiation angle of incidence.

2. Background Art

DE 197 20 874 C2 describes an optoelectronic sensor based on the disturbed total reflection of light principle. A first optical system (i.e., a first lens) parallelizes light from a transmitter and directs the light towards a coupler at a 45° input angle. The coupler couples the light into the internal side of the window at the 45° input angle. If the window is dry and clean, then light reaching the external side of the window is totally reflected back towards the coupler at a 45° output angle. The coupler decouples the reflected light (i.e., the useful light) towards a second optical system (i.e., a second lens) at the 45° output angle. The second lens directs the reflected light towards a receiver. Wetting of the window decouples the light from this optical path such that total reflection no longer takes place.

The coupler is a prism structure having a plurality of individual prisms. The prisms have prism surfaces in coupling areas arranged perpendicular to the 45° input angle and prism surfaces in decoupling areas arranged perpendicular to the 45° output angle. Each prism includes a side flank in addition to a prism surface. The flanks of the prisms extend perpendicular to the prism surfaces. As such, the prism flanks in the coupling areas are parallel with light transmitted into the window at the 45° input angle and the prism flanks in the decoupling areas are parallel with the useful light reflected from the window at the 45° output angle.

A problem is extraneous light influences cannot be completely excluded. Extraneous light reduces the sensitivity of such a sensor and may cause the sensor to trigger incorrectly. As such, a reduction in extraneous light results in a functional improvement of such a sensor.

Theoretical and experimental considerations identify an optical path on which extraneous light from the external environment can impinge on the receiver through the coupler and the second lens. Extraneous light incident at certain angles near the angle perpendicular to the window can impinge on the prism flanks and emerge glancing off these flanks. The second lens, which focuses the useful light reflected off the window towards the receiver, has an angular acceptance that is not insignificant; and the receiver includes an extensive surface. As a result, this extraneous light can reach the receiver.

SUMMARY OF THE INVENTION

An object of the present invention is an optoelectronic sensor for detecting moisture of a motor vehicle window (e.g., windshield) in which incident extraneous light coming through the window has a reduced influence on the receiver of the sensor.

In carrying out the above object and other objects, the present invention provides an optoelectronic sensor for detecting moisture on a pane. The sensor includes a transmitter for transmitting optical radiation towards a pane, and a receiver for receiving optical radiation reflected from the pane. The sensor further includes a coupler having prisms arranged in coupling areas for coupling optical radiation from the transmitter into the pane at a given input angle and a plurality of prisms arranged in decoupling areas for decoupling the optical radiation reflected from the pane out to the receiver at a corresponding given output angle. The prisms arranged in the coupling areas have prism surfaces arranged perpendicular to the given input angle and the prisms arranged in the decoupling areas have prism surfaces arranged perpendicular to the given output angle. Each prism includes a prism flank in addition to a prism surface.

In an embodiment, the prism flanks of the prisms arranged in the decoupling areas are arranged parallel to the given output angle and at least some of the prism flanks of the prisms arranged in the decoupling areas are opaque or roughened.

In an embodiment, at least some of the prism flanks of the prisms arranged in the decoupling areas are tilted from running parallel to the given output angle.

In an embodiment, the prism flanks of the prisms arranged in the decoupling areas are arranged parallel to the given output angle and at least some of the prism flanks of the prisms arranged in the decoupling areas include at least one additional prism superimposed on them.

An optoelectronic sensor in accordance with the present invention accomplishes the above object and other objects with a first aspect in which at least some of the prism flanks of the prisms of the coupler in the decoupling areas are roughened or made to be opaque.

An optoelectronic sensor in accordance with the present invention accomplishes the above object and other objects with a second aspect in which at least some of the prism flanks of the prisms of the coupler in the decoupling areas are tilted so that they are not parallel to the exit direction of the useful reflected light.

An optoelectronic sensor in accordance with the present invention accomplishes the above object and other objects with a third aspect in which at least some of the prism flanks of the prisms of the coupler in the decoupling areas have additional prisms superimposed on them.

Thus, an optoelectronic sensor in accordance with the present invention includes measures to reduce the proportion of exiting extraneous light glancing off the prism flanks (i.e., edges) of the coupler. This may be accomplished by roughening or covering the prism flanks (which are parallel to the useful light) of the prisms of the coupler, by tilting the prism flanks, or by additional deflection of the glancing exiting extraneous light with additional prisms superimposed on the prisms of the coupler.

BRIEF DESCRIPTION OF THE DRAWINGS

Three exemplary variants of an optoelectronic sensor in accordance with the present invention are explained in detail below with reference to the Figures in which.

DETAILED DESCRIPTION OF THE PREFERRED EMBODIMENT(S)

Figure 3:
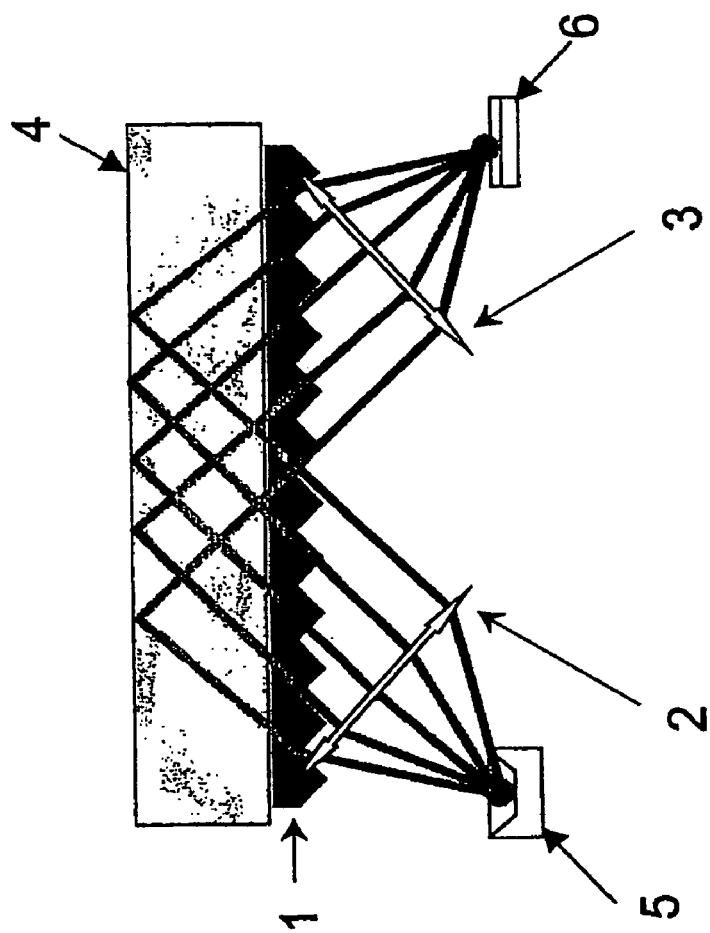
FIG. 3 illustrates functional principles of an optoelectronic sensor in accordance with the present invention.

Referring initially to FIG. 3, an optoelectronic sensor in accordance with the present invention is shown. The sensor senses rain, humidity, moisture, dirt, etc., on a pane 4. Pane 4 may be a window, windshield, glass pane, etc., of a motor vehicle. The sensor generally includes a light transmitter 5, a first lens 2, a coupler 1, a second lens 3, and a light receiver 6. The sensor is located on the interior side of pane 4. For instance, if pane 4 is a motor vehicle windshield, the sensor is located within the interior of the motor vehicle.

Light transmitter 5 includes a transmitting diode or the like for transmitting optical radiation. For instance, light transmitter 5 transmits optical radiation in the near infrared range at a wavelength of about 880 nm. Light receiver 6 includes a photodiode or the like for detecting optical radiation.

In operation, light transmitter 5 emits optical radiation towards first lens 2. First lens 2 converts the optical radiation into parallelized light and directs the light toward coupler 1 at a 45° input angle. Coupler 1, which is physically attached to the interior surface of the inner side of pane 4, couples the light into the internal side of pane 4 at the 45° input angle. The incident light coupled into pane 4 which reaches the external side of pane 4 is totally reflected back towards coupler 1 at a 45° output angle. Coupler 1 decouples the reflected light towards second lens 3 at the 45° output angle. Second lens 3 focuses and directs the reflected light onto light receiver 6.

If rain drops or dirt particles are present on the external surface of the external side of pane 4, then at this place part of the light impinging on pane 4 is decoupled out of pane 4 or absorbed. This causes a reduction in the intensity of the reflected light received by light receiver 6. This intensity change is indicative of the presence of rain drops or dirt particles on the external surface of the external side of pane 4.

The configuration of the sensor solves the problem of light coupling into pane 4 without refraction. Coupler 1 enables the solution of this problem. Coupler 1 includes a prism structure formed by a film, plastic, or glass body. The prism structure of coupler 1 includes a plurality of individual prisms. In the coupling areas, the prisms have prism surfaces arranged perpendicular to the light coupled into pane 4 (i.e., the prism surfaces are arranged perpendicular to the 45° input angle). In the decoupling areas, the prisms have prism surfaces arranged perpendicular to the light decoupled out of pane 4 (i.e., the prism surfaces are arranged perpendicular to the 45° output angle). As a result, the light passes into and out of coupler 1 without refraction.

Each prism includes a side flank in addition to a prism surface. The prism flanks extend perpendicular to the prism surfaces. As such, the prism flanks in the coupling areas are parallel with light transmitted into the window at the 45° input angle and the prism flanks in the decoupling areas are parallel with the useful light reflected from the window at the 45° output angle.

Figure 1:
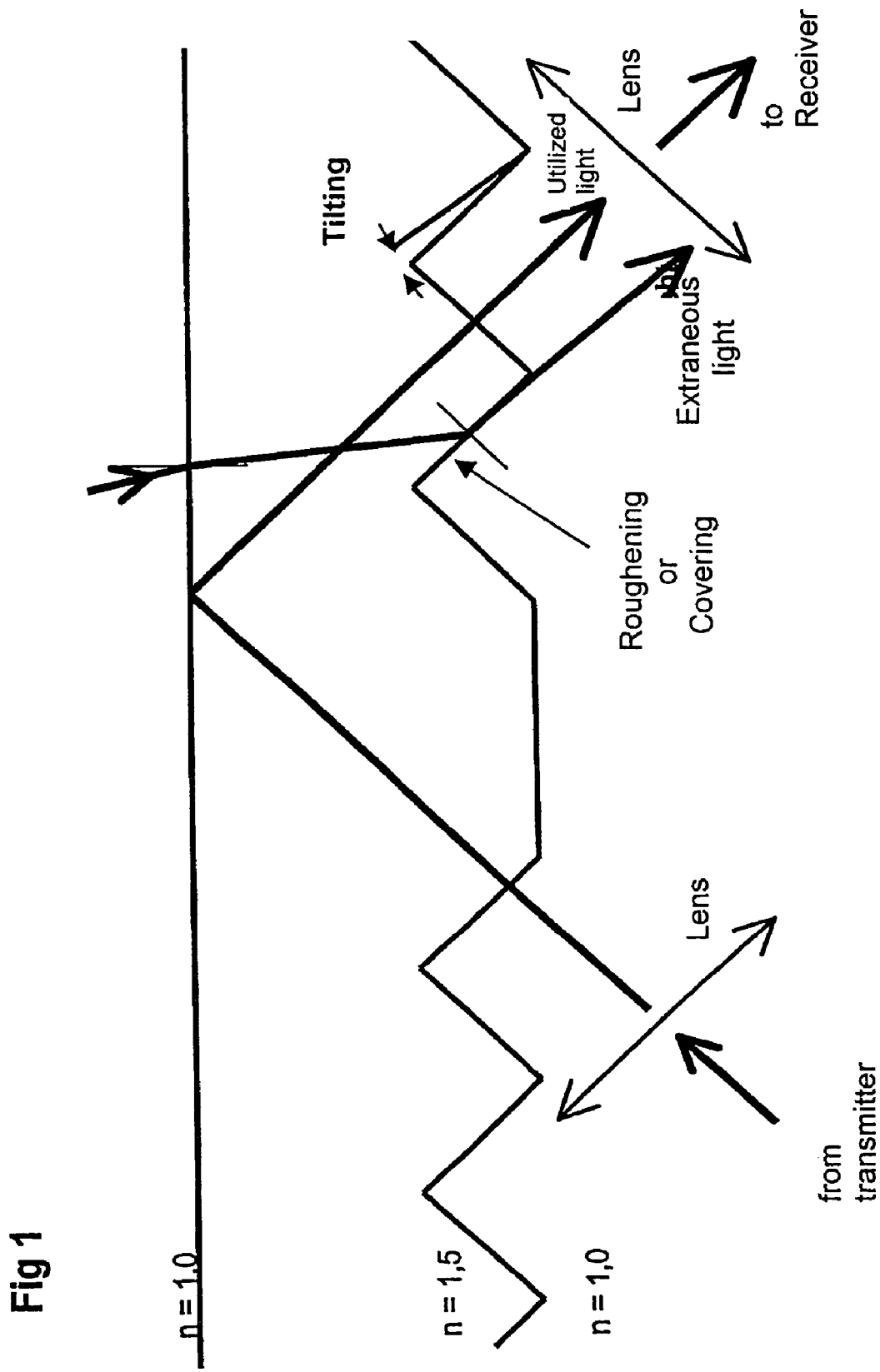
FIG. 1 illustrates an optoelectronic sensor in accordance with first and second embodiments of the present invention.
Figure 2:
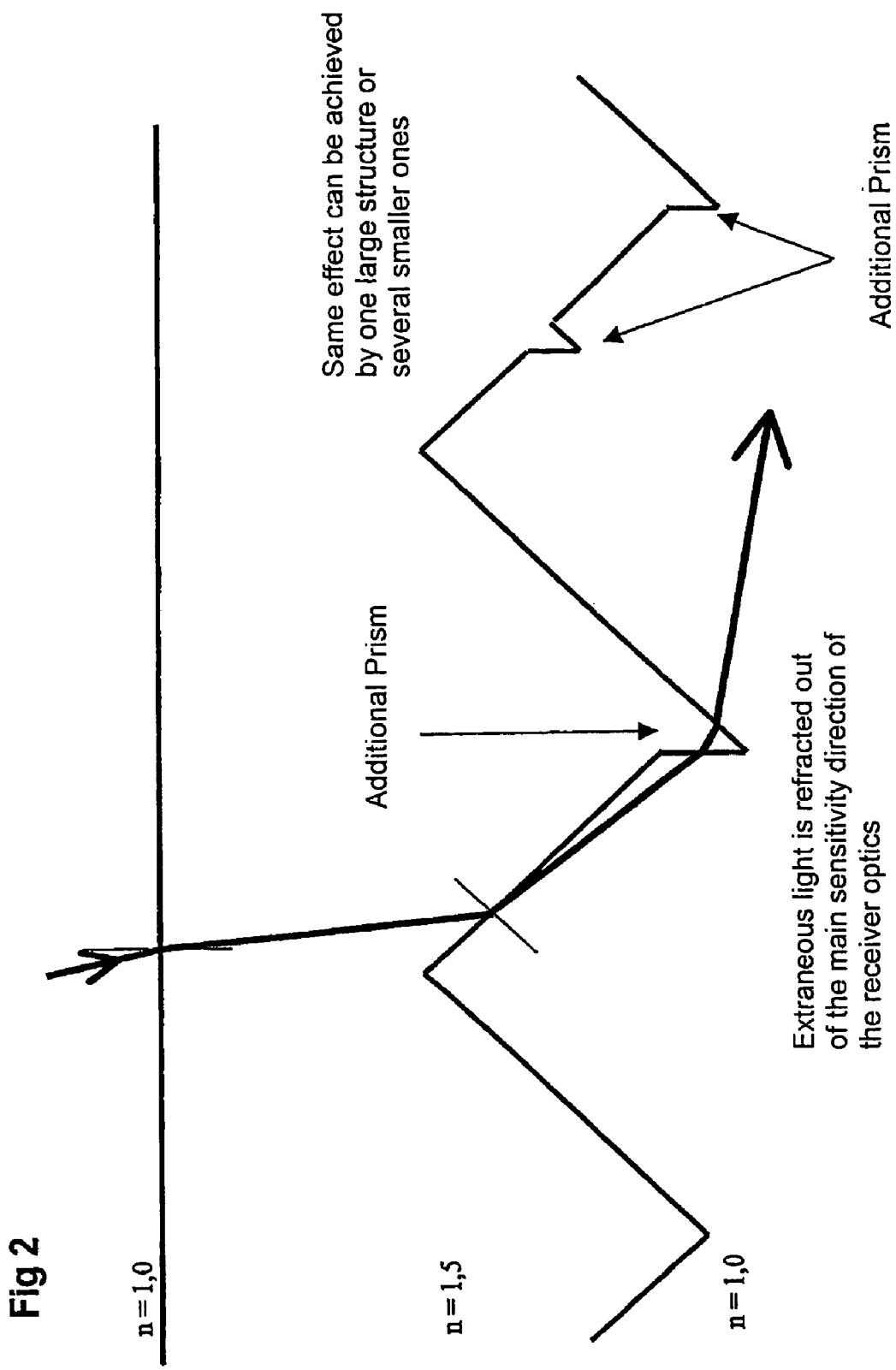
FIG. 2 illustrates an optoelectronic sensor in accordance with a third embodiment of the present invention.

Referring now to FIGS. 1 and 2, in conjunction with FIG. 3, three embodiments of an optoelectronic sensor in accordance with the present invention are shown. In general, the sensor in accordance with the present invention has a reduced sensitivity to extraneous light.

FIG. 1 in conjunction with FIG. 3 illustrates first and second embodiments of an optoelectronic sensor in accordance with the present invention. FIG. 2 in conjunction with FIG. 3 illustrates a third embodiment of an optoelectronic sensor in accordance with the present invention. FIGS. 1, 2, and 3 illustrate the prism structure of coupler 1, the external side of pane 4, and the part of the optical path on the side of light receiver 6.

Each sensor embodiment includes focusing receiver optics (i.e., second lens 3) in the optical path on the side of light receiver 6. Second lens 3 transforms the angle of the incident radiation into one place in the focal plane. As such, radiation emitted from light transmitter 5 which reflects off of pane 4 at the 45° output angle (i.e., the useful light) is projected by second lens 3 onto light receiver 6 while extraneous light from most other angles goes to other positions. As such, second lens 3 collects the useful light reflected off pane 4 and focuses this useful light onto light receiver 6 while extraneous light from most other angles goes to other positions.

However, extraneous light incident at certain angles which are at least nearly perpendicular to pane 4 can impinge on the prism flanks of the prism structure of coupler 1 and exit glancing off these prism flanks. As described above, the prism flanks are parallel to the useful light. As second lens 3 has an angular acceptance that is not insignificant and as light receiver 6 has an extensive surface, this extraneous light can undesirably reach light receiver 6.

With reference to FIG. 1, the sensitivity of the first optoelectronic sensor embodiment to extraneous light exiting from prism structure 1 by glancing off of the prism flanks toward light receiver 6 is reduced by covering or roughening the prism flanks in the decoupling areas. For instance, covering the prism flanks with paint or coating the prism flanks enables the prism flanks to absorb extraneous light reaching the prism flanks rather than allowing the extraneous light to glance off of the prism flanks. As a result, the extraneous light does not reach light receiver 6 as the extraneous light is absorbed by prism flanks. Hence, the sensitivity of the sensor to extraneous light is reduced.

Likewise, roughening the prism flanks enables the prism flanks to scatter the extraneous light into many different directions in space rather than allowing the extraneous light to glance off of the prism flanks. As a result, the part of the scattered extraneous light lying within the angular acceptance of second lens 3 and thus that of the surface of light receiver 6 is reduced. As a result, most of the extraneous light does not reach light receiver 6 as most of the extraneous light is scattered in different directions. Hence, the sensitivity of the sensor to extraneous light is reduced. The prism flanks can be roughened by erosion or etching structures put into an injection molding die of the prism structure of coupler 1.

In either instance of covering or roughening the prism flanks of the prism structure of coupler 1, only the prism flanks in the decoupling areas need to be covered or roughened. As such, the prism flanks in the coupling areas may be the same type of prism flanks of couplers in accordance with the background art. That is, the modification of the prism flank surfaces is only necessary for the optical path between coupler 1 and light receiver 6.

Again with reference to FIG. 1, the sensitivity of the second optoelectronic sensor embodiment to extraneous light exiting from prism structure 1 by glancing off of the prism flanks towards light receiver 6 is reduced by tilting the prism flanks in the decoupling areas by a few degrees (a maximum of about 5°) with respect to the nominal angle of 45°. This causes the extraneous light to glance off of the tilted prism flanks at the titled angle relative to the nominal 45° angle. The nominal 45° angle is the main acceptance direction of second lens 3. That is, the receiving characteristics of second lens 3 prefer the main direction of 45° and attenuates radiation incident at other angles. Thus, this also attenuates the extraneous light reaching light receiver 6. Hence, the sensitivity of the sensor to extraneous light is reduced. Again, this modification of the prism flank surfaces is only necessary for the optical path between coupler 1 and light receiver 6.

Another variant of an optoelectronic sensor in accordance with the present invention includes prism flanks which are covered or roughened and tilted in the manners described above.

With reference to FIG. 2, the sensitivity of the third optoelectronic sensor embodiment to extraneous light exiting from prism structure 1 by being refracted off of the prism flanks towards light receiver 6 is reduced by adding additional prism edges to the prism flanks in the decoupling areas. The additional prism edges deflect glancing exiting extraneous light from the receiving direction path of light receiver 6. This can involve superimposing on the prism flanks of coupler 1 either individual large additional prism edges or several smaller ones. To a great extent, the additional prisms can have any shape but do not have sharp edges. For example, the additional prisms can advantageously be in the form of half cylinders.

While embodiments of the present invention have been illustrated and described, it is not intended that these embodiments illustrate and describe all possible forms of the present invention. Rather, the words used in the specification are words of description rather than limitation, and it is understood that various changes may be made without departing from the spirit and scope of the present invention.

What is claimed is:

1. A sensor for detecting moisture on a pane, the sensor comprising:
   a transmitter for transmitting optical radiation towards a pane;
   a receiver for receiving optical radiation reflected from the pane;
   a coupler having a plurality of prisms arranged in coupling areas for coupling optical radiation from the transmitter into the pane at a given input angle and a plurality of prisms arranged in decoupling areas for decoupling the optical radiation reflected from the pane out to the receiver at a corresponding given output angle, wherein the prisms arranged in the coupling areas have prism surfaces arranged perpendicular to the given input angle and the prisms arranged in the decoupling areas have prism surfaces arranged perpendicular to the given output angle;
   wherein each prism includes a prism flank in addition to a prism surface, wherein the prism flanks of the prisms arranged in the decoupling areas are arranged parallel to the given output angle;
   wherein at least some of the prism flanks of the prisms arranged in the decoupling areas are opaque.

2. The sensor of claim 1 wherein:
   at least some of the prism flanks of the prisms arranged in the decoupling areas are roughened.

3. The sensor of claim 2 wherein:
   the roughened prism flanks are roughened by sandblasting.

4. The sensor of claim 2 wherein:
   the coupler includes injection-molded plastic and the roughened prism flanks are roughened by structuring in the injection mold.

5. The sensor of claim 1 wherein:
   the coupler includes plastic.

6. The sensor of claim 1 wherein:
   the opaque prism flanks are painted to be opaque.

7. The sensor of claim 1 wherein:
   the opaque prism flanks include an opaque material adhered thereon.

8. The sensor of claim 1 wherein:
   at least some of the prism flanks arranged in the decoupling areas are mirrors.

9. The sensor of claim 8 wherein:
   the mirror prism flanks include a metal coating thereon.

10. The sensor of claim 1 wherein:
    the coupler is physically attached to an interior surface of an inner side of the pane and the transmitter and the receiver are both located adjacent to the inner side of the pane.

11. The sensor of claim 10 wherein:
    the pane is the windshield of a motor vehicle and the sensor is located within the motor vehicle interior.

12. The sensor of claim 1 wherein:
    the given input angle is 45° and the corresponding given output angle is 45°.

13. A sensor for detecting moisture on a pane, the sensor comprising:
    a transmitter for transmitting optical radiation towards a pane;
    a receiver for receiving optical radiation reflected from the pane;
    a coupler having a plurality of prisms arranged in coupling areas for coupling optical radiation from the transmitter into the pane at a given input angle and a plurality of prisms arranged in decoupling areas for decoupling the optical radiation reflected from the pane out to the receiver at a corresponding given output angle, wherein the prisms arranged in the coupling areas have prism surfaces arranged perpendicular to the given input angle and the prisms arranged in the decoupling areas have prism surfaces arranged perpendicular to the given output angle;
    wherein each prism includes a prism flank in addition to a prism surface, wherein at least some of the prism flanks of the prisms arranged in the decoupling areas are tilted from running parallel to the given output angle.

14. The sensor of claim 13 wherein:
    at least some of the prism flanks of the prisms in the decoupling areas are arranged parallel to the given output angle.

15. The sensor of claim 13 wherein:
    the titled prism surfaces have a maximum angular deviation 5° with respect to the given output angle.

16. The sensor of claim 13 wherein:
    the coupler is physically attached to an interior surface of an inner side of the pane and the transmitter and the receiver are both located adjacent to the inner side of the pane.

17. The sensor of claim 16 wherein:
    the pane is the windshield of a motor vehicle and the sensor is located within the motor vehicle interior.

18. A sensor for detecting moisture on a pane, the sensor comprising:
- a transmitter for transmitting optical radiation towards a pane;
- a receiver for receiving optical radiation reflected from the pane;
- a coupler having a plurality of prisms arranged in coupling areas for coupling optical radiation from the transmitter into the pane at a given input angle and a plurality of prisms arranged in decoupling areas for decoupling the optical radiation reflected from the pane out to the receiver at a corresponding given output angle, wherein the prisms arranged in the coupling areas have prism surfaces arranged perpendicular to the given input angle and the prisms arranged in the decoupling areas have prism surfaces arranged perpendicular to the given output angle;
- wherein each prism includes a prism flank in addition to a prism surface, wherein the prism flanks of the prisms arranged in the decoupling areas are arranged parallel to the given output angle;
- wherein at least some of the prism flanks of the prisms arranged in the decoupling areas include at least one additional prism superimposed on them.

19. The sensor of claim 18 wherein:
the coupler is physically attached to an interior surface of an inner side of the pane and the transmitter and the receiver are both located adjacent to the inner side of the pane.

20. The sensor of claim 18 wherein:
the pane is the windshield of a motor vehicle and the sensor is located within the motor vehicle interior.

* * * * *